(12) United States Patent
Ariga

(10) Patent No.: US 8,318,798 B2
(45) Date of Patent: Nov. 27, 2012

(54) THERAPEUTIC AGENT FOR NEURODEGENERATIVE DISEASE

(75) Inventor: Hiroyoshi Ariga, Hokkaido (JP)

(73) Assignee: National University Corporation Hokkaldo University, Hokkaldo (JP)

( * ) Notice: Subject to any disclaimer, the term of this patent is extended or adjusted under 35 U.S.C. 154(b) by 1098 days.

(21) Appl. No.: 12/085,424

(22) PCT Filed: Nov. 17, 2006

(86) PCT No.: PCT/JP2006/322977
§ 371 (c)(1),
(2), (4) Date: Jul. 22, 2008

(87) PCT Pub. No.: WO2007/060886
PCT Pub. Date: May 31, 2007

(65) Prior Publication Data
US 2009/0233872 A1 Sep. 17, 2009

(30) Foreign Application Priority Data

Nov. 24, 2005 (JP) .................................. 2005-339011
Sep. 5, 2006 (JP) .................................. 2006-240421

(51) Int. Cl.
*A61K 31/36* (2006.01)
*A61K 31/12* (2006.01)
*A61K 31/04* (2006.01)
(52) U.S. Cl. .......................... 514/466; 514/679; 514/741
(58) Field of Classification Search .................. 514/466, 514/679, 741
See application file for complete search history.

(56) References Cited

U.S. PATENT DOCUMENTS

| 4,960,759 A | 10/1990 | De Luca et al. | |
|---|---|---|---|
| 2004/0014947 A1* | 1/2004 | Ogi et al. | 530/350 |

FOREIGN PATENT DOCUMENTS

| EP | 0 490 818 | 6/1992 |
|---|---|---|
| GB | 1308259 | 2/1973 |
| JP | 47-21438 | 6/1972 |
| JP | 56-102794 A | 8/1981 |
| JP | 2-45425 | 2/1990 |
| JP | 03-038553 A | 2/1991 |
| JP | 4-290895 | 10/1992 |
| JP | 2000-503668 | 3/2000 |
| WO | WO-97/45127 | 12/1997 |
| WO | 2006122090 A2 | 11/2006 |

OTHER PUBLICATIONS

Intelihealth, "Parkinson's disease," online, accessed Sep. 22, 2009, http://www.intelihealth.com/IH/ihtIH?d=dmtHealthAZ&c=201957.*
Miyazaki S, Yanagida T, Nunome K, Ishikawa S, Inden M, Kitamura Y, Nakagawa S, Taira T, Hirota K, Niwa M, Iguchi-Ariga SM, Ariga H.. DJ-1-binding compounds prevent oxidative stress-induced cell death and movement defect in Parkinson's disease model rats. J Neurochem. Jun. 1, 2008;105(6):2418-34.*
Pursiainen V, Haapaniemi TH, Korpelainen JT, Huikuri HV, Sotaniemi KA, Myllylä VV. Circadian heart rate variability in Parkinson's disease. J Neurol. Nov. 2002;249(11):1535-40.*
Roden DM, Chapter 35 Antiarrhythmic Drugs, "Goodman & Gilman's The Pharmacological Basis of Therapeutics, 10th ed." Hardman JG, Limbird LE, and Gilman AG, Eds., McGraw-Hill, 2001, 933-970 (pp. 933 and 953 provided).*
Inden et al., Neurobiology of Disease, 24:144-158 (2006).
Kametani et al., Neurobiology, Journal of the Chemical Society, No. 16, pp. 1954-1957 (1974).
Takahashi-Niki et al., Biochemical and Biophysical Research Communications, 320:389-397 (2004).
Taira et al., EMBO Reports, 5(2):213-218 (2004).
Deumens et al., Experimental Neurology, 175:303-317 (2002).
Swerdlow et al., Annals of Neurology, 40(4):663-671 (1996).
Bonifati et al., Science, 299:256-259 (2003).
Rego et al., Neurochemical Research, 28(10):1563-1574 (2003).
Tretter et al., Neurochemical Research, 29(3):569-577 (2004).
Huang et al., J. Org. Chem., 42(24):3821-3824 (1977).
Holy, Collection Czechoslovak Chem. Commun., 47:2786-2805 (1982). I.
Michel et al., Journal of Neurochemistry, 72(5):2074-2082 (1999).
R.J. Borgman et al., "Synthesis and Pharmacology of Centrally Acting Dopamine Derivatives and Analogs in Relation to Parkinson's Disease", Journal of Medicinal Chemistry, 16(6), pp. 630-633 (1973).
J. Xu et al., "The Parkinson's disease-associated DJ-1 protein is a transcriptional co-activator that protects against neuronal apoptosis", Human Molecular Genetics, 14(9), pp. 1231-1241 (2005).
European Search Report, mailed May 25, 2012, in corresponding European Patent Application No. EP 11006919.2.
P.P. Michel et al., "Adenosine Prevents the Death of Mesencephalic Dopaminergic Neurons by a Mechanism that Involves Astrocytes", Journal of Neurochemistry, 72(5), pp. 2074-2082 (1999).
Office Action from corresponding Japanese Application No. 2007-546418, dated Jul. 31, 2012.

\* cited by examiner

*Primary Examiner* — Paul Zarek
(74) *Attorney, Agent, or Firm* — Peter F. Corless; Christine C. O'Day; Edwards Wildman Palmer LLP

(57) ABSTRACT

[Problems] To provide a neuronal cell death inhibitor and a therapeutic agent for a neurodegenerative disease, particularly Parkinson's disease.
[Means for Solving Problems] It is known that DJ-1 protein is involved in Parkinson's disease and is capable of inhibiting neuronal cell death caused by oxidative stress. Based on this knowledge, screening is made for a low molecular weight molecule capable of binding to an active site of DJ-1 protein (i.e., a region around a cysteine residue at position-106) using an analysis softwear FastDock (Fujitsu Ltd.). When various tests are made using candidate low molecular weight compounds each having a binding energy of −60 kcal/mol or lower, these compounds show a therapeutic effect on a neurodegenerative disease.

2 Claims, 8 Drawing Sheets

[FIG. 1]
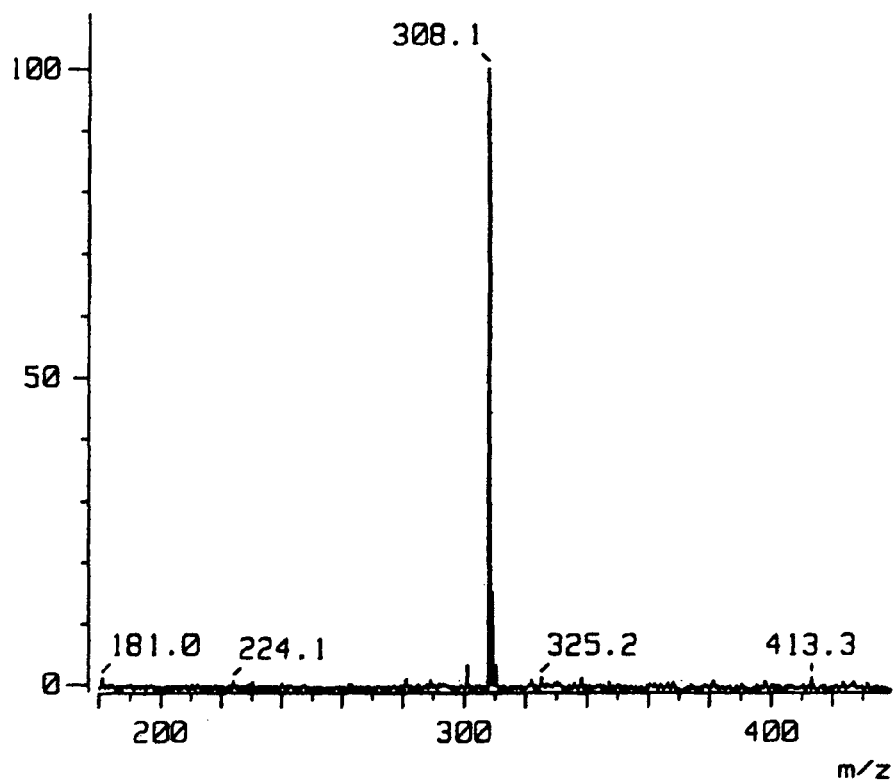
[FIG. 2]
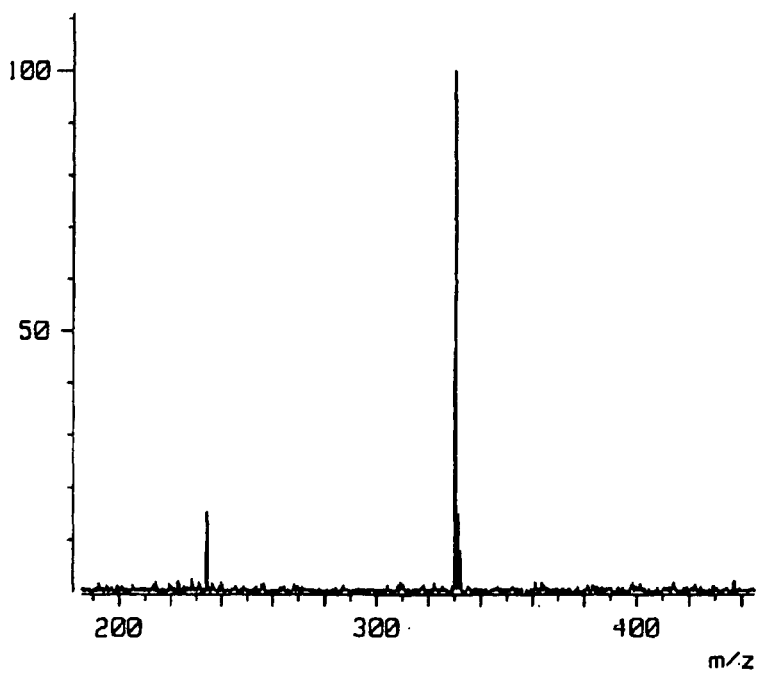

[FIG. 3]
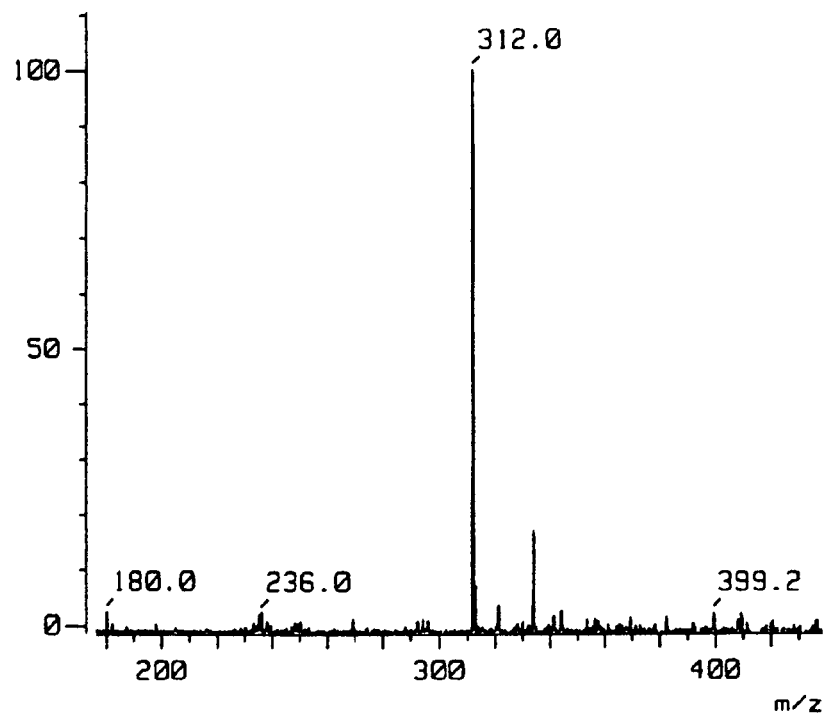
[FIG. 4]
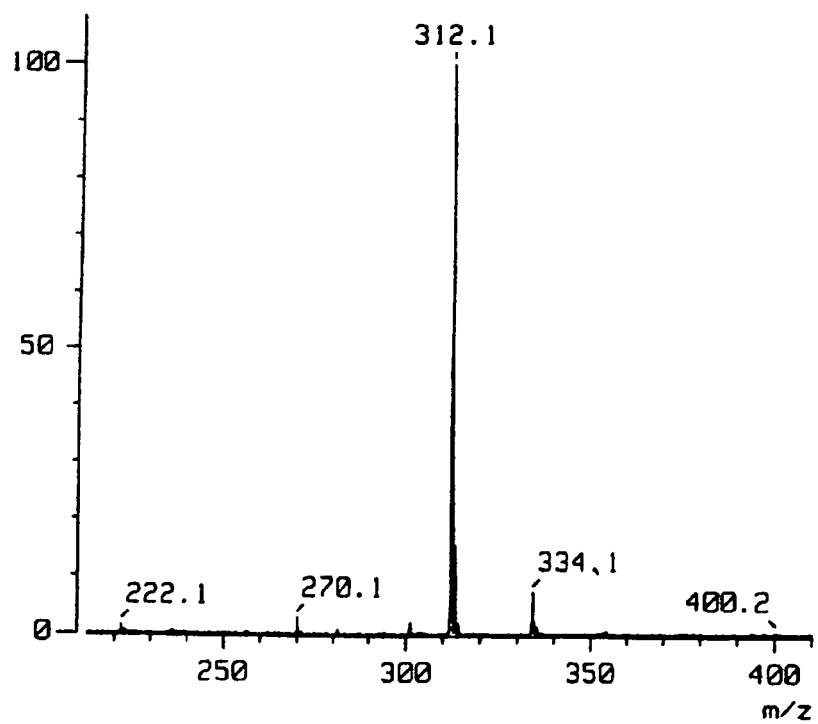

[FIG. 5]
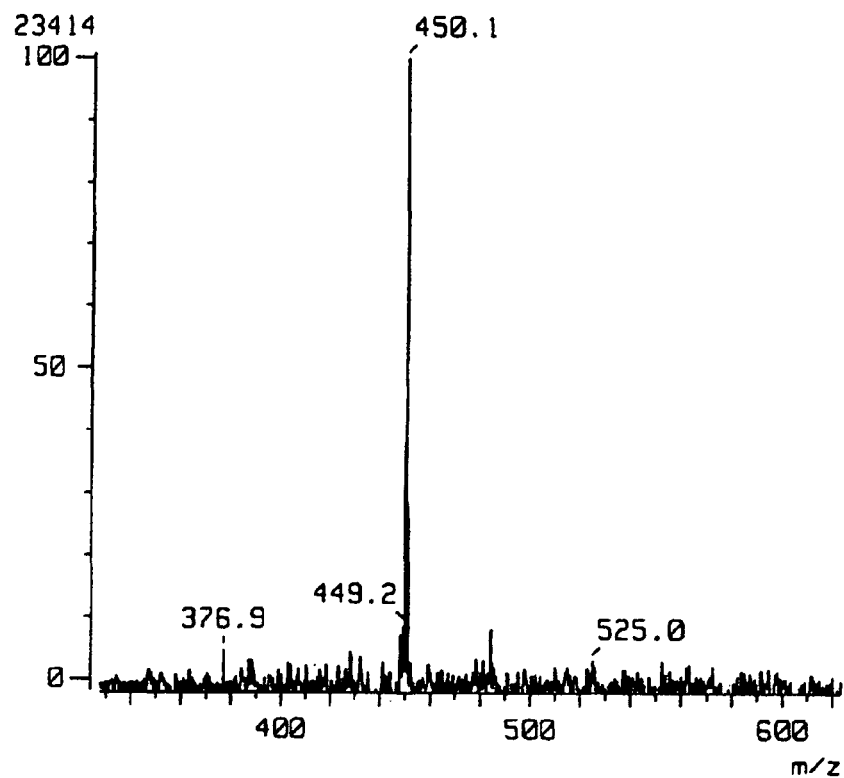
[FIG. 6]
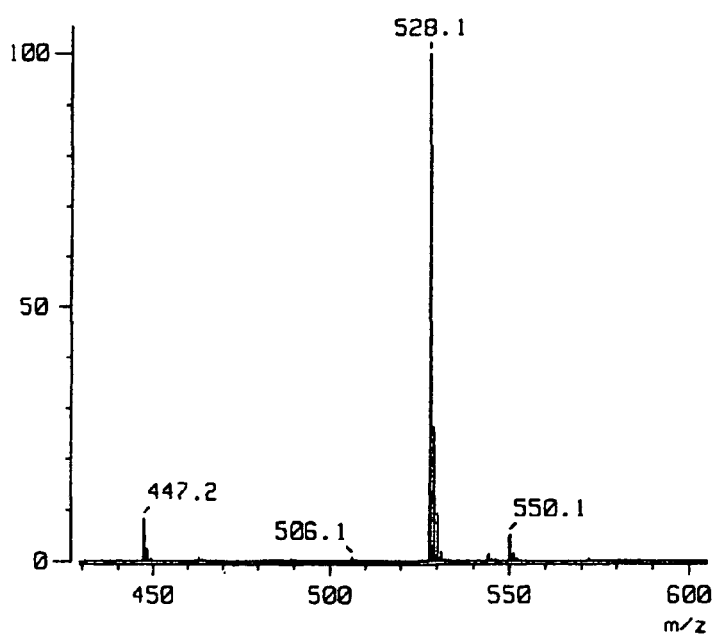

[FIG. 7]
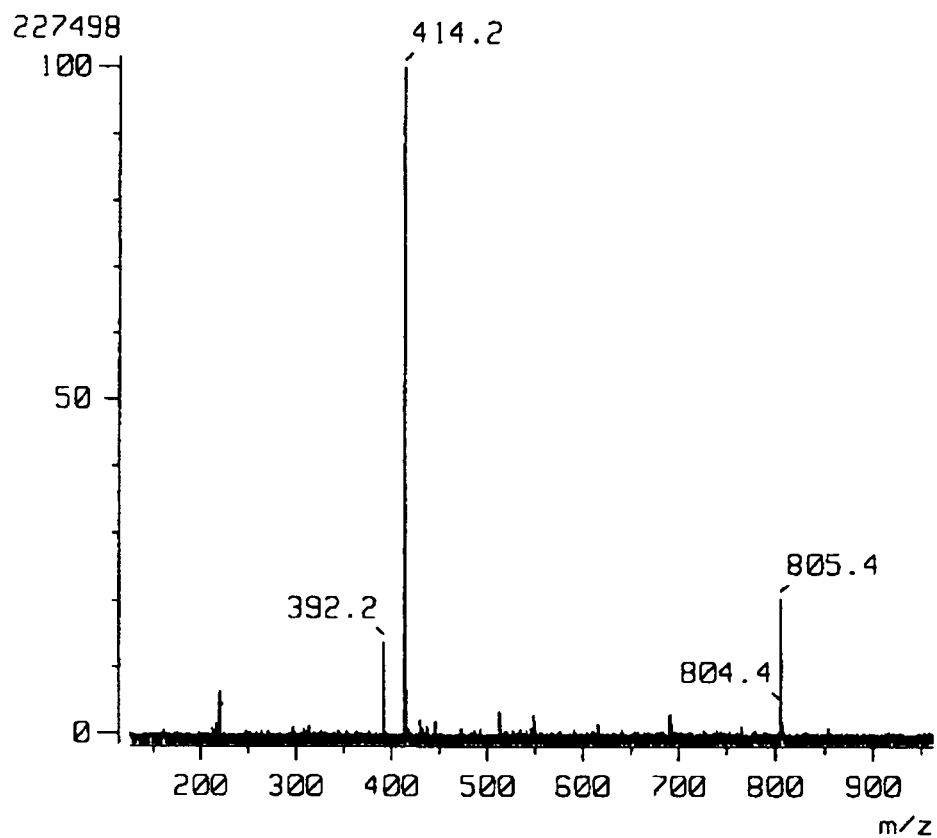
[FIG. 8]
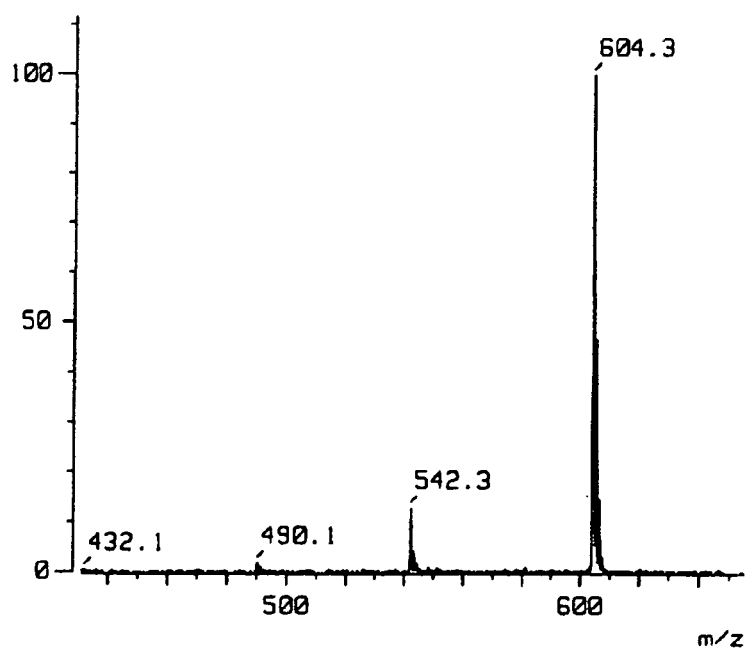

[FIG. 9]
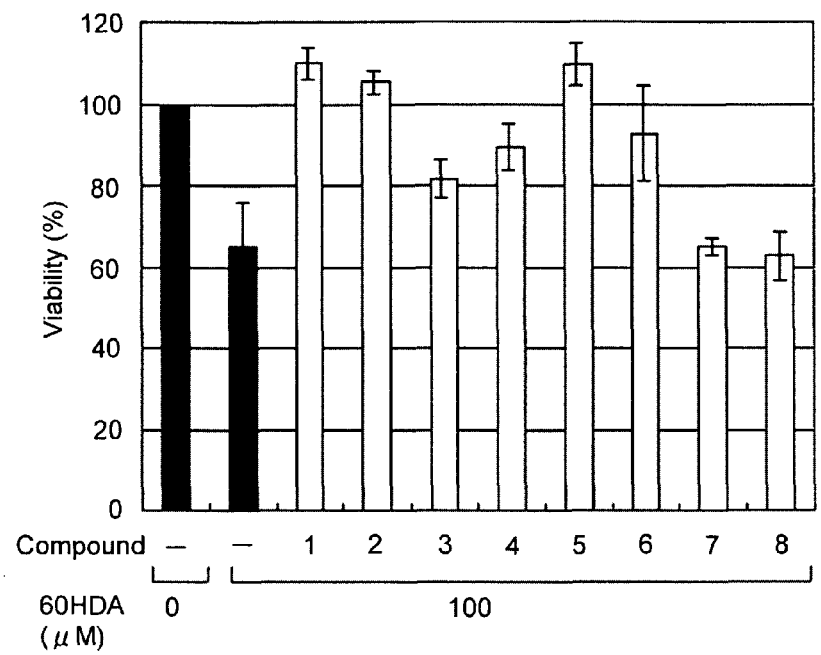
[FIG. 10]
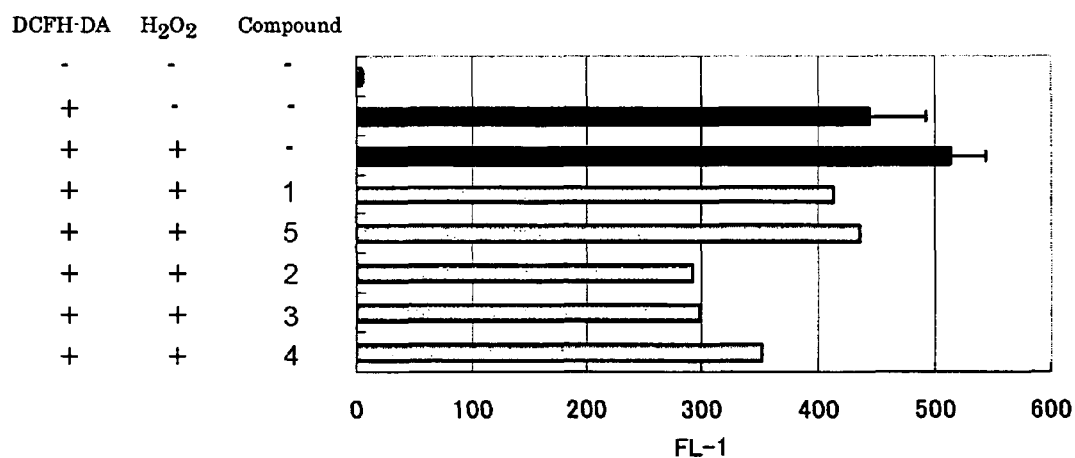

[FIG. 11]
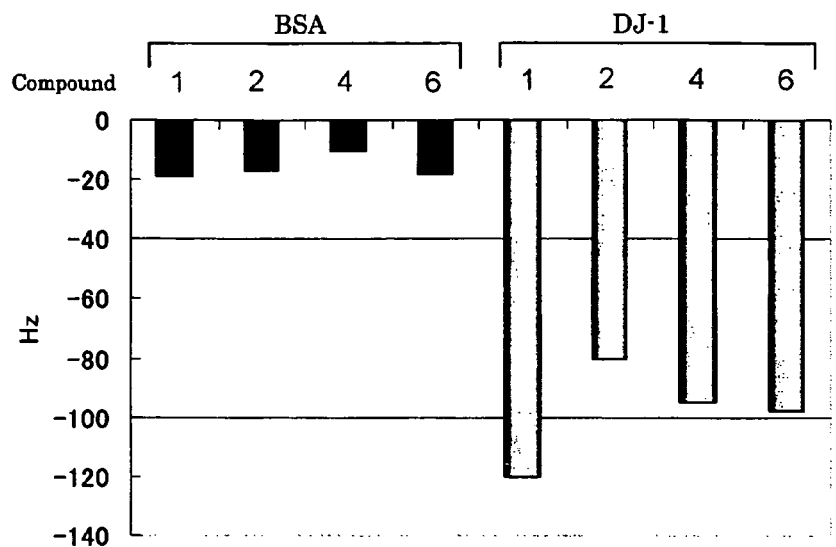
[FIG. 12]
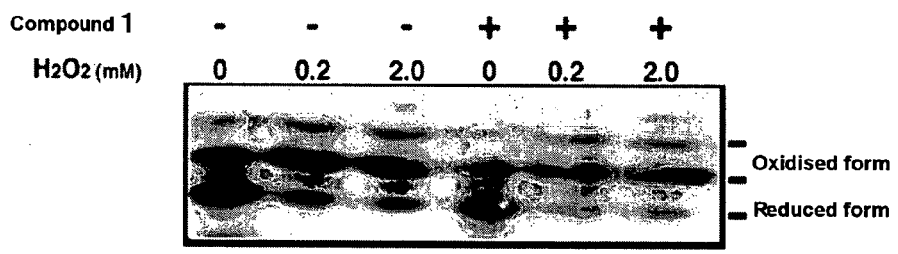
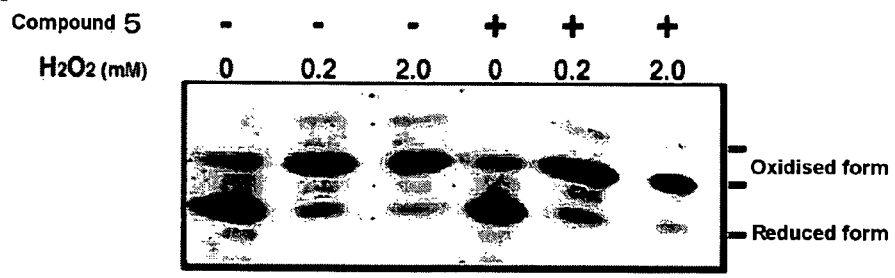
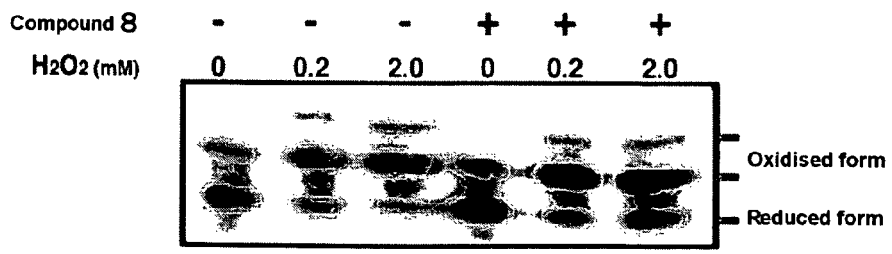

[FIG. 13]
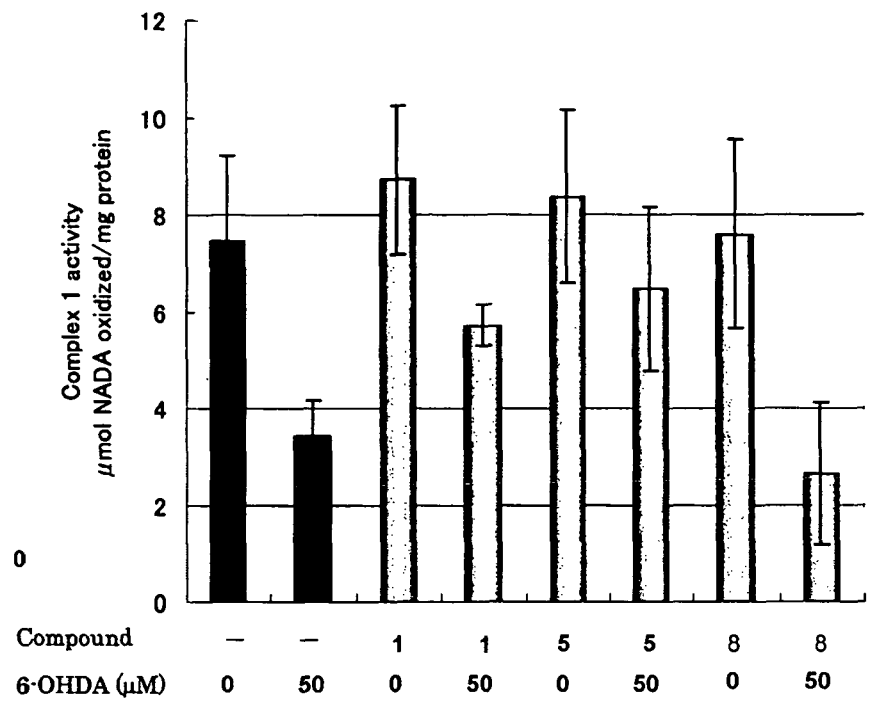
[FIG. 14]
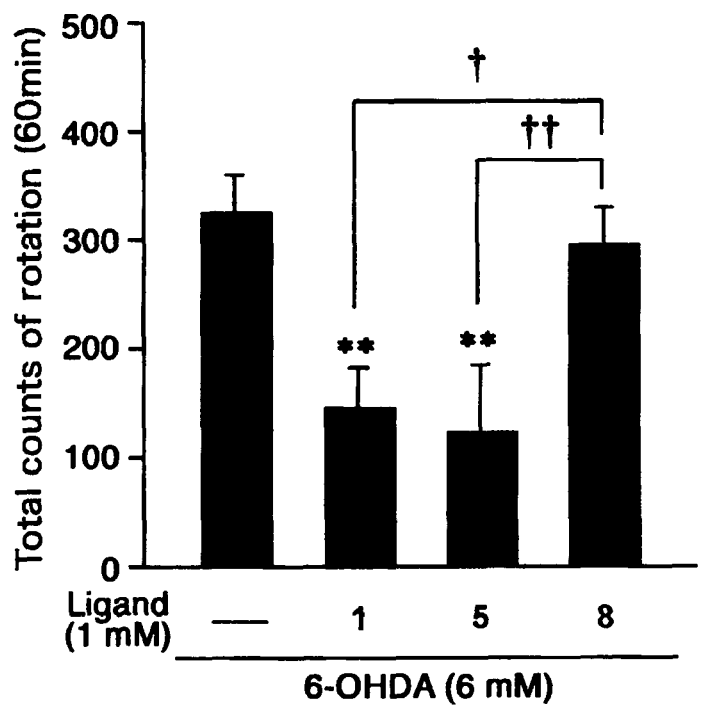
** p<0.01 vs. 6-OHDA alone
† p<0.05, †† p<0.01 vs. 6-OHDA + C

[FIG. 15]
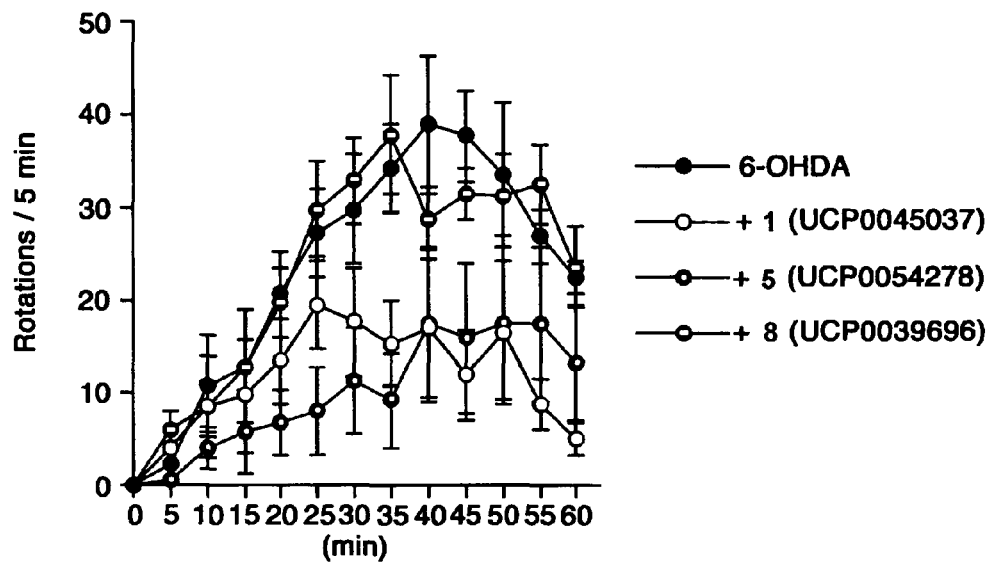
[FIG. 16]
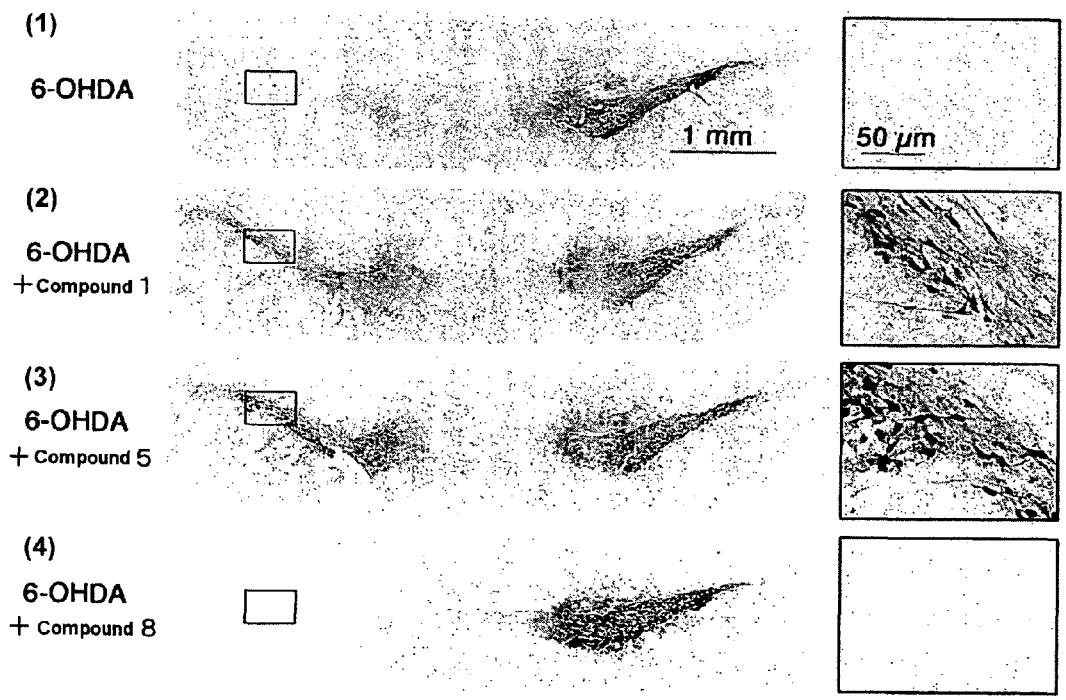

THERAPEUTIC AGENT FOR NEURODEGENERATIVE DISEASE

TECHNICAL FIELD

The present invention relates to a therapeutic agent for a neurodegenerative disease and, more particularly, to a drug for treating Parkinson's disease.

BACKGROUND ART

In Parkinson's disease, the death of the midbrain dopamine neurons induces a decrease in the amount of dopamine released into the striatum, disrupting the balance between dopamine and acetylcholine in the striatum, thereby developing dyskinesia.

It has also been confirmed that Parkinson's disease is caused by oxidative stress and inhibition of mitochondrial complex I (Nonpatent Publications 1 to 3), suggesting that Parkinson's disease can be treated by suppressing oxidative stress and inhibition of mitochondrial complex I.

Currently employed methods for the treatment of Parkinson's disease are divided roughly into four as follows.

1) Dopamine replacement therapy. Since dopamine itself has low blood-brain barrier (BBB) permeability, L-dopa (levodopa), a dopamine precursor that has a high BBB permeability, is administered. Although L-dopa exhibits an excellent effect at initial stages of administration, L-dopa itself may give an oxidative stress on neurons, and may adversely aggravate the symptoms.

2) Administration of a drug that suppresses the dopamine degradation system. For example, selegiline is known as a drug for inhibiting monoamine oxidase, MAO, which is involved in dopamine degradation.

3) Administration of a drug that activates dopamine transporter, which is present at the striatum membrane and has the function of uptaking dopamine into the striatum.

4) Administration of a drug (such as trihexyphenidyl) that suppresses the acetylcholine production by suppressing the function of cholinergic neurons in a hyperexcited state.

However, since these therapeutic methods are palliative treatments for the decrease in the amount of dopamine due to neuronal death, there is a desire for a therapeutic method that suppresses neuronal death itself.

DJ-1 protein, on the other hand, is present in a wide range of human cells including neurons, and consists of 189 amino acids. DJ-1 protein is an oncogene product, being known to be involved in PARK7 (familial Parkinson's disease) (Nonpatent Publication 4).

Furthermore, it is known that DJ-1 protein has an effect in suppressing neuronal death caused by oxidative stress. It has been reported that, when a Parkinson's disease model rat that has been injected with 6-hydroxydopamine, which gives oxidative stress, is injected with DJ-1 protein simultaneously with or after the injection of the 6-hydroxydopamine, the death of dopamine neurons is suppressed, and behavioral abnormality is improved (Nonpatent Publication 5).

It has also been reported that a DJ-1 protein C106 variant (106th amino acid residue being altered from cysteine to serine) does not suppress the death of dopamine neuronal in a Parkinson's disease model rat (Nonpatent Publications 6 and 7).

[Nonpatent Publication 1]
Neurochem. Res. 2004 March, 29 (3); 569-577
[Nonpatent Publication 2]
Neurochem. Res. 2003 October, 28 (10); 1563-1574
[Nonpatent Publication 3]
Annals of Neurol. 1996 October, 40 (4); 663-671
[Nonpatent Publication 4]
Science, 2003 January, 299 (5604); 256-9
[Nonpatent Publication 5]
Experimental Neurology, 2002, 175; 303-317
[Nonpatent Publication 6]
EMBO Reports, 2004 February, 5 (2); 213-8.
[Nonpatent Publication 7]
Biochem. Biophys. Res. Commun., 2004 Jul. 23, 320 (2); 389-97.

DISCLOSURE OF INVENTION

Problems to be Solved by the Invention

The object of the present invention is to provide an agent for suppressing neuronal death and a therapeutic agent for a neurodegenerative disease, in particular, a drug for treating Parkinson's disease.

Means for Solving the Problems

In order to attain the object above, DJ-1 protein has come to the attention of the present inventors. It has been known that DJ-1 protein is involved in Parkinson's disease (Nonpatent Publication 4), has an effect in suppressing neuronal death caused by oxidative stress (Nonpatent Publication 5), and, furthermore, the C106 variant DJ-1 protein does not suppress the death of dopamine neurons in a Parkinson's disease model rat (Nonpatent Publications 6 and 7).

The activity of DJ-1 is regulated by the oxidation state of the cysteine at the 106th residue (C106). It transits from —SH (reduced form) to the $SO_2H$ and $SO_3H$ oxidized forms according to the degree of oxidation, of which DJ-1 in the forms of the former two are active (in particular, the $SO_2H$ form has the highest activity), whereas the $SO_3H$ form is inactive.

From this, the inventors considered that a low molecular weight compound that binds to the active site of DJ-1 protein (that is, the region around the cysteine at the 106th residue) would bind to the —SH and $SO_2H$ forms, inhibit the transition to $SO_3H$, and thereby maintain the active form of DJ-1. The present inventors, therefore, screened for candidate compounds using FastDock analysis software (made by FUJITSU).

Several candidate low molecular weight compounds were used to calculate their binding strength to the active site of DJ-1 protein, from which low molecular weight compounds having a certain high degree of binding strength (binding energy) were selected and actually subjected to various assays (see Examples below).

Consequently, it has been found that compounds having a binding energy of a specific value or below (e.g. −60 kcal/mol or below) exhibit an effect in suppressing neuronal death and an effect in treating neurodegenerative disease, and the present invention has thus been accomplished.

The compound of the present invention is considered to have an effect in suppressing neuronal death caused by oxidative stress of DJ-1 protein.

The present invention is a therapeutic agent for a neurodegenerative disease comprising as a main component a compound represented by General Formulae (Formulae 1) below

[Chem. 1]

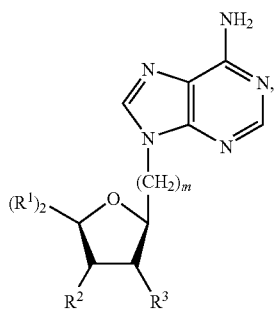

(1)

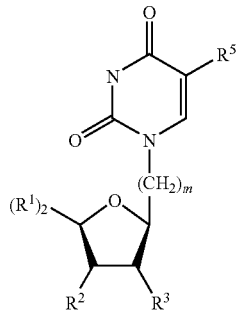

(2)

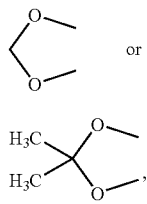

(3)

(wherein, $R^1$ may be identical to or different from each other and denote a hydrogen atom, an alkyl group having 1 to 6 carbons, a hydroxymethyl group, or a siloxymethyl group (—CH$_2$—O—SiR$^6_3$, R$^6$ denotes an alkyl group having 1 to 6 carbons or an aryl group), or two R$^1$s together denote an oxygen atom (=O), R$^2$ and R$^3$ may be identical to or different from each other and denote a hydroxy group, an alkoxy group, an aryloxy group, an acyloxy group (—O—CO—R$^7$, R$^7$ denotes an alkyl group having 1 to 6 carbons or an aryl group), or a sulfonyloxy group (—O—SO$_2$—R$^8$, R$^8$ denotes an alkyl group having 1 to 6 carbons or an aryl group), or alternatively R$^2$ and R$^3$ may together form Formulae (Formulae 2) below

[Chem. 2]

(1)

(2)

m denotes 0 or 1, R$^4$ denotes a hydrogen atom or an acetyl group, and R$^5$ denotes a hydrogen atom, a hydroxy group, or a nitro group).

Furthermore, the present invention is a therapeutic agent for a neurodegenerative disease comprising as a main component a compound represented by General Formula (Formula 3) below

[Chem. 3]

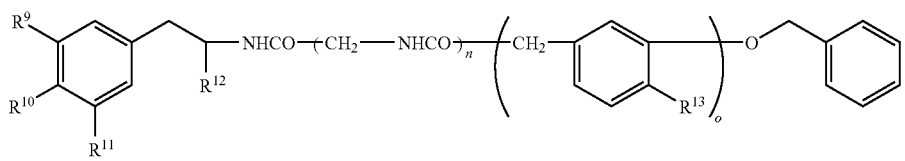

(wherein, $R^9$ to $R^{11}$ may be identical to or different from each other and denote a hydrogen atom, a hydroxy group, an alkoxy group, an aryloxy group, an acyloxy group (—O—CO—R$^{14}$, R$^{14}$ denotes an alkyl group having 1 to 6 carbons or an aryl group) or a sulfonyloxy group (—O—SO$_2$—R$^{15}$, R$^{15}$ denotes an alkyl group having 1 to 6 carbons or an aryl group), or alternatively R$^9$ and R$^{10}$ may together form Formulae (Formulae 2) below

[Chem. 2]

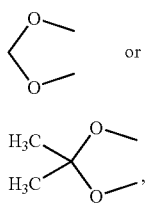

(1)

(2)

$R^{12}$ denotes a hydrogen atom or —(CONH)$_p$R$^{16}$ (wherein, R$^{16}$ denotes an alkyl group, an aryl group, or —CH(CONH$_2$)$_q$(CH$_2$SO$_2$NH$_2$)$_r$(CH$_2$CH(CH$_3$)$_2$)$_s$ (wherein, q, r, and s denote integers of 0 to 2 that satisfy q+r+s=2), and p denotes 1 or 2), R$^{13}$ denotes a hydrogen atom, a hydroxy group, or an alkoxy group, n denotes an integer of 0 to 2, and o denotes 0 or 1).

Effects of the Invention

According to the present invention, a drug for causal treatment is provided, which has a different mechanism from that of a symptomatic treatment drug, the conventional therapeutic agent for a neurodegenerative disease. In particular, a novel therapeutic or prophylactic agent or for Parkinson's disease is provided.

BEST MODE FOR CARRYING OUT THE INVENTION

The compound of the present invention is represented by the Formulae (Formulae 1) below, of which (1) is preferable. These compounds have a common structure containing a purine or pyrimidine residue and a sugar residue, and distinctions between these compounds do not make a marked difference in binding to the active site of DJ-1 protein.

[Chem. 1]

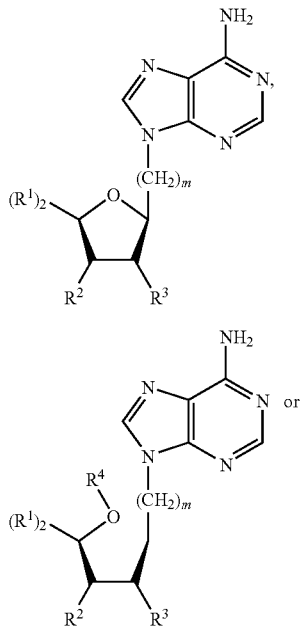

(1)

(2)

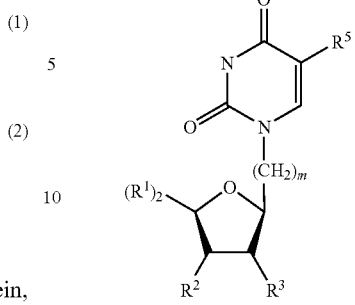

(3)

$R^1$ may be identical to or different from each other and denote a hydrogen atom, an alkyl group having 1 to 6 carbons, a hydroxymethyl group (—CH$_2$OH), or a siloxymethyl group, or two R$^1$'s together denote an oxygen atom (=O), and it is preferable that one thereof denotes a hydrogen atom and the other denotes a hydroxymethyl group.

This siloxymethyl group is represented by —CH$_2$—O—SiR$^6$$_3$, wherein R$^6$ denotes an alkyl group having 1 to 6 carbons or an aryl group, and preferably an alkyl group having 1 to 6 carbons. This alkyl group is preferably a methyl group, and the aryl group is preferably a phenyl group.

$R^2$ and $R^3$ may be identical to or different from each other, and denote a hydroxy group, an alkoxy group, an aryloxy group, an acyloxy group, or a sulfonyloxy group, and preferably a hydroxy group.

This alkoxy group is preferably an alkoxy group having 1 to 6 carbons, and the aryloxy group is preferably a phenoxy group.

This acyloxy group is represented by —O—CO—R$^7$, wherein R$^7$ denotes an alkyl group having 1 to 6 carbons or an aryl group, and preferably an alkyl group having 1 to 6 carbons. This alkyl group is preferably a methyl group, and the aryl group is preferably a phenyl group.

This sulfonyloxy group is represented by —O—SO$_2$—R$^8$, wherein R$^8$ denotes an alkyl group having 1 to 6 carbons or an aryl group, and preferably an alkyl group having 1 to 6 carbons. This alkyl group is preferably a methyl group, and the aryl group is preferably a phenyl group.

Furthermore, $R^2$ and $R^3$ may together form Formulae (Formulae 2) below,

[Chem. 2]

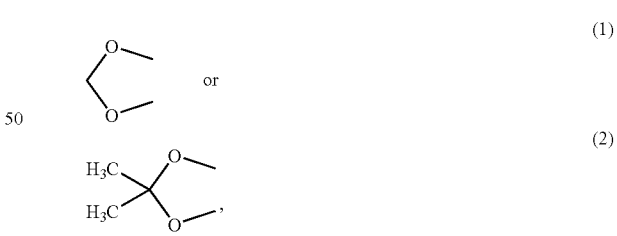

(1)

(2)

and they preferably together form Formula (Formulae 2) (1).

m denotes 0 or 1, and preferably 0.

$R^4$ denotes a hydrogen atom or an acetyl group (—COCH$_3$), and preferably an acetyl group.

$R^5$ denotes a hydrogen atom, a hydroxy group, or a nitro group (—NO$_2$), and preferably a nitro group.

Another compound of the present invention is represented by Formula (Formula 3) below. This compound has a characteristic structure such that a benzene ring and two-carbon skeleton attached thereto are linked to a peptide bond, and distinctions between compounds represented by this general formula do not make a marked difference in binding to the active site of DJ-1 protein.

[Chem. 3]

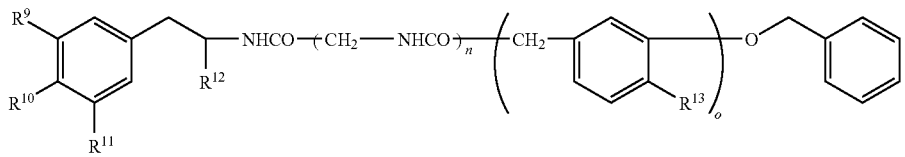

$R^9$ to $R^{11}$ may be identical to or different from each other, and denote a hydrogen atom, a hydroxy group, an alkoxy group, an aryloxy group, an acyloxy group, or a sulfonyloxy group.

The acyloxy group is represented by —O—CO—$R^{14}$, wherein $R^{14}$ denotes an alkyl group having 1 to 6 carbons or an aryl group, and preferably an alkyl group having 1 to 6 carbons. This alkyl group is preferably a methyl group, and the aryl group is preferably a phenyl group.

The sulfonyloxy group is represented by —O—$SO_2$—$R^{15}$, wherein $R^{15}$ denotes an alkyl group having 1 to 6 carbons or an aryl group, and preferably an alkyl group having 1 to 6 carbons. This alkyl group is preferably a methyl group, and the aryl group is preferably a phenyl group.

Among $R^9$ to $R^{11}$, preferably at least one, more preferably at least two, and most preferably all thereof are hydrogen atoms.

$R^9$ and $R^{10}$ may together form Formulae (Formulae 2) below,

[Chem. 2]

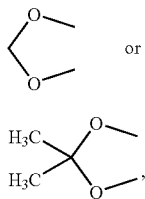

and they preferably together form Formula (Formulae 2) (1).

$R^{12}$ denotes a hydrogen atom or —$(CONH)_p R^{16}$, and preferably —$(CONH)_p R^{16}$, and p denotes 1 or 2, and preferably 1. In the formula, $R^{16}$ denotes an alkyl group, an aryl group, or —$CH(CONH_2)_q(CH_2SO_2NH_2)_r(CH_2CH(CH_3)_2)_s$ and preferably —$CH(CONH_2)_q(CH_2SO_2NH_2)_r(CH_2CH(CH_3)_2)_s$. The alkyl group is preferably an alkyl group having 1 to 6 carbons, and the aryl group is preferably a phenyl group. In this formula, q, r, and s independently denote integers of 0 to 2 that satisfy q+r+s=2, and q is preferably 1. $R^{12}$ is represented by, for example, Formula (Formula 4) below.

[Chem. 4]

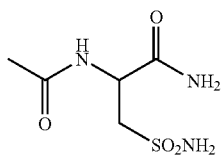

$R^{13}$ denotes a hydrogen atom, a hydroxy group, or an alkoxy group, and is preferably a hydrogen atom. The alkoxy group is preferably a methoxy group.

n denotes an integer of 0 to 2, and preferably 0 or 1.

o denotes 0 or 1, and preferably 0.

Whether or not a candidate compound binds to the active site of DJ-1 protein (i.e. the region around the cysteine at the 106th residue) was determined based on the binding energy of a complex between the DJ-1 protein and the candidate compound using virtual screening by computer based on the structure of the active site of DJ-1 protein as described below.

This virtual screening was carried out using FastDock analysis software (made by FUJITSU). This FastDock is software for calculating the binding energy between a protein and a candidate compound using an evaluation function known as the extended PMF method. A BioServer (manufactured by FUJITSU) was used as hardware.

The binding energy of the complex was calculated based on the PMF (Protein Mean Force) method. The PMF method is a method for predicting the binding energy between a protein and a ligand by statistical analysis using a three-dimensional structure database; a protein-ligand (compound) complex is configured, and the total interaction energy for all pairs of atoms in the configured complex is determined. The PMF method used in this virtual screening is a method employing the Lennard-Jones potential.

The virtual screening comprises the following steps.

First step: obtaining information on optimized structure of active site of DJ-1 protein.

Second step: obtaining information on structure of target compound.

Third step: determining binding energy of complex between the compound and the active site of the optimized structure while altering the structural conformer of the compound (docking step).

First Step

Information on the optimized structure of the active site of DJ-1 protein is obtained by 1) obtaining X-ray structural analysis information for the entire DJ-1 protein, 2) modifying the molecular structure using the information thus obtained and optimizing the overall structure, and 3) setting the C106 region of DJ-1 protein as the active site. X-ray structural information for the entire DJ-1 protein was obtained from J. Biol. Chem. 278, pp. 31380 (2003). Examples of processing for modifying the molecular structure of the entire DJ-1 protein from the X-ray structural information obtained as above include hydrogen addition and water molecule processing. Hydrogen addition processing, in which a hydrogen atom is added to the X-ray structure read in, is necessary for obtaining an optimized structure that reflects hydrogen bonding. In water molecule processing, the tertiary structure of the entire DJ-1 protein is obtained in a state where it contains water molecules in solvent and within the protein, then the water molecules within the protein is removed to give an optimized structure. The water molecule processing enables the binding energy between the complex and a compound to be calculated based on direct binding between the DJ-1 protein and the compound, while taking into consideration the influence of water molecules on the optimized structure.

Second Step

A two-dimensional structure of a compound is read in from an sdf file contained in a compound library, and a three-dimensional structure is obtained by correcting the position of hydrogen by means of molecular mechanics calculation.

Third Step

In the docking step, while changing the three-dimensional structure of a target compound, the binding energy of a complex between each conformer of the compound and the active site of the optimized structure is calculated, and the lowest binding energy is determined. Changing the three-dimensional structure means changing spatial configuration of the compound while changing the torsion of its bonds, thus generating various conformers.

It has been found from these calculations and the Examples below that a low molecular weight compound whose binding energy with the DJ-1 active site is −60 kcal/mol or below, and particularly −90 kcal/mol or below, has an effect in suppressing neuronal death and an effect in treating a neurodegenerative disease.

It is considered that, when the binding energy between the active site and the low molecular weight compound is −60 kcal/mol or below, and particularly −90 kcal/mol or below, strong binding is maintained, and, transition of DJ-1 to the over-oxidized —$SO_3H$ form is suppressed as described in the Examples below, resulting an enhanced bioactivity of DJ-1, and suppressing the neuronal death caused by oxidative stress.

The compound of the present invention, upon administering to a living body such as a human, eliminates active oxygen within neurons and suppresses cell death thereof, thus functioning as a neuronal death inhibitor and a therapeutic agent for a neurodegenerative disease. This may be because the compound of the present invention binds to DJ-1 protein and enhances the antioxidant action of DJ-1 protein as shown in the Examples below.

A therapeutic agent for a neurodegenerative disease for suppressing the death of dopamine neurons is preferably be able to pass through the blood-brain barrier. In general, a compound that has a nucleic acid structure can pass through the blood-brain barrier. Therefore, a compound containing a purine or pyrimidine residue and a sugar residue, as with the compound of the present invention, can be used preferably as a therapeutic agent for a neurodegenerative disease.

Examples of the neurodegenerative disease for which the compound of the present invention can be used as a therapeutic agent include Parkinson's disease, Alzheimer's disease, Huntington's chorea, ALS, and apoplexy. It is preferably used for Parkinson's disease. It is thought that a cause of onset of these neurodegenerative diseases is neuronal death due to oxidative stress, and the compound of the present invention acts effectively.

The concentration of the compound of the present invention contained in the therapeutic agent for a neurodegenerative disease is not particularly limited. The therapeutic agent for a neurodegenerative disease of the present invention may contain any component in addition to the compound as long as the effects of the present invention are not impaired. A method for administering the therapeutic agent for a degenerative disease of the present invention is not particularly limited (oral administration, administration by injection, etc.), and neither is its form particularly limited (powder, tablet, injection solution, etc.).

EXAMPLES

The present invention is illustrated below by reference to Examples, but they are not intended to limit the present invention.

Production Example 1

Compounds 1 to 6 with the formulae below were prepared as compounds that bind to the DJ-1, compound 7 with the formula below as a compound with low binding strength to DJ-1, and compound 8 with the formula below as a compound that does not bind to DJ-1 to be used in the Examples.

[Chem. 5]

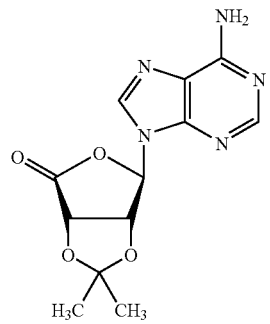

1

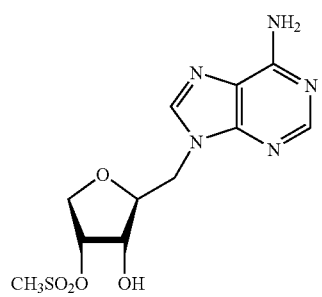

2

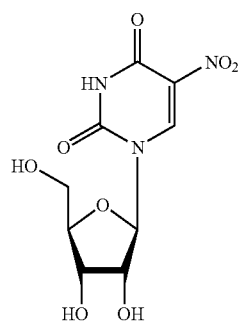

3

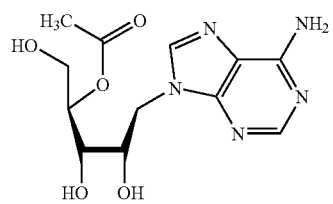

4

[Chem. 6]

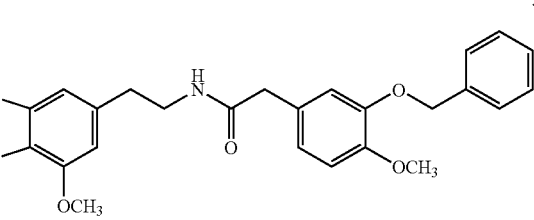

5

-continued

6

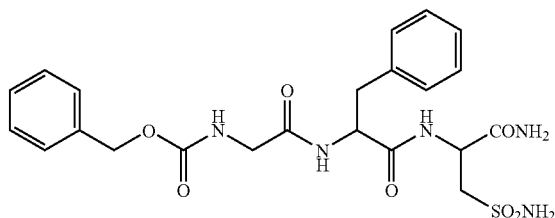

[Chem. 7]

7

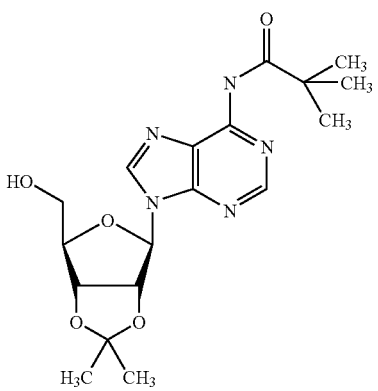

8

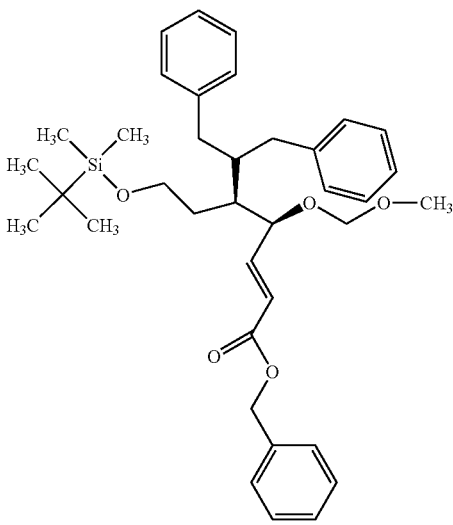

Sources or production processes of the compounds:
Compounds 1 to 4 and 7: Prof. Kosaku Hirota, Laboratory of Mechanical Chemistry, School of Pharmacy, Aichi Gakuin University.
Compound 5: Prof. Toshio Honda, Faculty of Pharmaceutical Science, Hoshi University.
Compound 6: Prof. Hristo Daskalov, Medicinal Chemistry, University of Sofia.
Compound 8: Prof. Yoshiteru Oshima, Laboratory of Natural Products Chemistry, Graduate School of Pharmaceutical Science, Tohoku University.
Compound 5: The phenethylamine (I) of the formula below (1.0 mol) was dissolved in benzene, and the carboxylic acid (II) of the formula below (1.1 mol) was gradually added thereto at room temperature. This solution was stirred until the starting materials disappeared, and after treatments such as filtration and washing with water, the product was purified by silica gel column chromatography, thereby giving the corresponding amide as colorless crystals in a yield of 70%.

[Chem. 8]

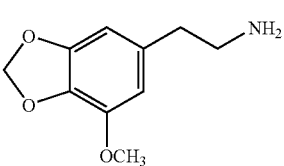 (I)

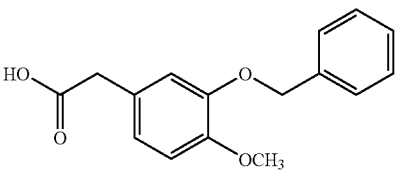 (II)

Compound 6: 862 mg of L-phenylalanine methyl ester hydroxychloride (Fluka Chemical) was dissolved in 0.2 M maleic acid buffer, and the pH was adjusted to 6.7 using 0.5 N sodium hydroxide. 10 mg of thermolysin (Fluka Chemical) was added thereto, and 418 mg of benzyloxycarbonylglycine (Fluka Chemical) was further added thereto. The reaction solution was mixed for 3 hours, thus giving 2-(2-benzyloxycarbonylaminoacetylamino)-3-phenylpropionate methyl ester.

370 mg of the 2-(2-benzyloxycarbonylaminoacetylamino)-3-phenylpropionate methyl ester was dissolved in 50 mL of methyl alcohol, and the solution was made alkaline using sodium hydroxide and mixed at room temperature overnight. After the pH was further adjusted to 7.0 using hydrochloric acid, crystals of 2-(2-benzyloxycarbonylaminoacetylamino)-3-phenylpropionic acid were precipitated by evaporation.

712 mg of the 2-(2-benzyloxycarbonylaminoacetylamino)-3-phenylpropionic acid was dissolved in 10 mL of 0.2 M bicarbonate buffer, and the pH was adjusted to 9.3 using 5 N hydrochloric acid. 24 mg of α-chymotrypsin (Fluka Chemical) was added thereto, and 334 mg of L-cysteinesulfonamide (Fluka Chemical) was further added thereto. The reaction solution was mixed for 2 hours and then filtered, thus giving the product.

These compounds are registered in The University Compound Data Base built by the Foundation for Education of Science and Technology, and are available from the Foundation.

Each compound was subjected to mass spectroscopy (Electrospray (ESI) mass spectra) under the conditions below. The equipment used and the conditions were as follows: JMS-700TZ (JEOL, Tokyo, Japan) four-sector (BE/BE) tandem mass spectrometer. Typical measurement conditions were as follows: acceleration voltage, 5.0 kV; needle voltage, 3.24 kV; orifice 1 voltage, 0.0 kV; ring lens voltage, 60.0 V; desolvation temperature, 80° C.; orifice 1 temperature, 230° C.; sample flow rate, 22 μL/min; solvent, chloroform. For sample injection, a syringe pump (Harvard PHD 2000 Advanced Syringe Pump, Harvard Apparatus, Holliston, Mass.) was used. Mass spectra were recorded in the positive ion mode within m/z 100-1500.

Mass spectrum charts of compounds 1 to 8 are shown in FIGS. 1 to 8.

The binding energies of complexes with the active site of DJ-1 protein (i.e. the region around the cysteine at the 106th residue) obtained using FastDock analysis software (made by FUJITSU) were −91.3 kcal/mol (compound 1), −101.9 kcal/mol (compound 2), −98.1 kcal/mol (compound 3), −97.9 kcal/mol (compound 4), −103.4 kcal/mol (compound 5), −102.91 kcal/mol (compound 6), −56.3 kcal/mol (compound 7), and +209.9 kcal/mol (compound 8).

Example 1

In this example, the effect of compounds 1 to 8 in suppressing cell death of SH-SY5Y human neurons was examined.

SH-SY5Y human neurons (American Tissue Culture Collection, USA) were plated on a 96-well plate, and cultured to 80% confluency.

Compounds 1 to 8 in sterile aqueous solutions were individually added thereto at a sample concentration of 1 μM, or sterile water was added as a control.

24 hours after the addition of compounds 1 to 8 or sterile water, 6-hydroxydopamine (PBS solvent) (Wako Pure Chemical Industries, Ltd.) was added to each at a 6-hydroxydopamine concentration of 100 μM, or the same amount of PBS (containing no 6-hydroxydopamine) was added. Furthermore, 40 hours after the addition of 6-hydroxydopamine, Cell Counting Kit-8 was added for carrying out an MTT assay.

After 3 hours, a viable cell count was measured by measuring the absorbance at wavelength of 450 nm. For each of compounds 1 to 8 and the control, the viability was obtained from '(the viable cell count when 6-hydroxydopamine was added)/(the viable cell count when no 6-hydroxydopamine was added)'.

FIG. 9 shows the viability when compounds 1 to 8 or sterile water (control) were added. Compared with the control and compounds 7 and 8, it can be seen that the addition of any one of compounds 1 to 6 enhances the viability.

Example 2

In this example, the effect of compounds 1 to 5 in eliminating hydrogen peroxide was examined.

SH-SY5Y human neurons were plated onto a 10 cm dish and cultured to 80% confluency. Compounds 1 to 5 individually were added at a concentration of 10 μM, or sterile water was added. 24 hours after the addition of the compounds or sterile water, hydrogen peroxide was added at a concentration of 50 μM. 1 hour after the addition of hydrogen peroxide, the fluorescent dye DCFH-DA (Dichlorofluorescein diacetate) was added, and incubated for 15 minutes. The cells were collected, the fluorescence intensity was measured by FACS, and the amount of hydrogen peroxide in the cells was determined.

The measurement results are shown in FIG. 10. In all cases, it can be seen that when the compound and hydrogen peroxide were added, the fluorescence intensity was weak, that is, the amount of hydrogen peroxide was small, compared with a case in which only hydrogen peroxide was added.

Example 3

In this example, by using an AffinixQ (Initium Inc.) it was confirmed that compounds 1, 2, 4, and 6 bind to DJ-1 protein.

The AffinixQ is an instrument for quantifying interaction between biomolecules at the order of nanograms by changes in frequency of the crystal oscillator. It utilizes the proportional relationship between change in frequency of the quartz oscillator and the weight of the adherings on the surface of the quartz oscillator.

The compound was fixed on top of the sensor chip, which is the oscillator, using an amino coupling reagent. The sensor chip onto which the compound had been fixed was immersed in a measurement vessel filled with 8 mL of PBS (phosphate buffer), and held until the frequency became constant. Following this, 8 μL of 1 mg/mL DJ-1 protein or BSA (bovine serum albumin) was added to the measurement vessel.

The results of measurement of frequency changes are shown in FIG. 11. When DJ-1 was added, the frequency greatly decreased compared with a case in which BSA was added, suggesting that the compound was bound to the DJ-1.

Example 4

In this example, it was confirmed that compound 1 and compound 5 suppressed the transition of DJ-1 to an oxidized form.

0.5 mg of purified DJ-1 protein was dissolved in 1 mL of PBS. 10 μL of 1 mM compound 1, 5, or 7 was added to 500 μL of this DJ-1 protein solution, and rotated at 4° C. for 1 hour. Subsequently, 0.4 or 4 mM hydrogen peroxide ($H_2O_2$) was added thereto, the mixture was allowed to stand at room temperature for 1 hour then the hydrogen peroxide concentration became 0.2 mM or 2 mM. Further, dialysis was carried out 3 times with PBS for a total of 4.5 hours, followed by an isoelectric focusing 0.5 μg of the DJ-1 protein. The reagents used in the isoelectric focusing were as follows.

Gel solution for isoelectric focusing: 9.2 M Urea, 2% NP-40, 4% acrylamide, 1% Ampholine (pH 5-8; Amersham Bioscience), 1% Ampholine (pH 3-10; Amersham Bioscience)

Sample Buffer: 5 M Urea, 2 M ThioUrea, 2% NP-40, 5% Glycerin, 5% 2-mercaptoethanol, 1.6% Ampholine (pH 5-8), 0.4% Ampholine (pH 3.5-10)

Protection solution: 8 M Urea, 0.8% Ampholine (pH 5-8), 0.2% Ampholine (pH 3.5-10)

Electrophoresis Buffer+electrode: 0.02 M Phosphoric acid −electrode: 0.02 M NaOH Towbin: 25 mM Tris, 192 mM Glycine The electrophoresis results are shown in FIG. 12. It can be seen that, compound 1 and compound 5 suppressed the transition of DJ-1 protein to an oxidized form compared with compound 8.

Example 5

In this example, the effect of compounds 1, 5, and 8 in maintaining the activity of mitochondrial complex 1 was examined.

6-Hydroxydopamine induces oxidative stress by degrading the enzymic activity of Complex 1 and thereby causing a functional disorder. It is considered that the compounds identified here would suppress neuronal death due to oxidative stress by preventing deactivation of complex 1. Therefore, changes in activity of complex 1 resulting from addition of the compound was measured.

SH-SY5Y human neurons were plated onto a 10 cm dish and cultured to 80% confluency. Compounds 1, 5, and 8 individually were added at the compound concentration of 1 μM, or sterile water was added. 24 hours after the addition of the compound or sterile water, 6-hydroxydopamine (PBS solvent) was added at a 6-hydroxydopamine concentration of 50 μM, or the same amount of PBS (containing no 6-hydroxydopamine) was added. 6 hours after the addition of 6-hydroxydopamine, the cells were collected. This cell suspension was disrupted in ice 80 times using a Potter homogenizer. This homogenate was centrifuged at 4° C. and 800×g for 8 minutes, the supernatant thereof was further centrifuged at 4° C. and 11000×g for 30 minutes, the supernatant was removed, and 200 μL of 0.25 M sucrose was added to the pellet, which was defined as a mitochondrial fraction. After quantifying the protein, 100 μg of the mitochondrial protein was added to a cuvette filled with a reaction buffer, and the total amount was made up to 480 μL. After incubation at 37° C. for 3 minutes, 20 μL of 5 mM NADH was added to the cuvette, and decrease in absorbance at 340 nm was monitored for 4 minutes using an absorptiometer.

The composition of the reaction buffer and the method for calculating Complex 1 activity are described below.

Reaction buffer: 6.65 mM $NaH_2PO_4$, 28.35 mM $Na_2HPO_4$, 5 mM $MgCl_2$, 5 mM EDTA, 1 mg/mL BSA, 2 ng/mL antimycine, 50 μM ubiquinone 1, 2.65 mM NaCN Complex 1 activity(μmol NADH oxidized/mg protein)
=$\Delta A340/4/6.22 \times 1000 \times 0.5/0.1$ ΔA340: difference in absorbance at 340 nm between beginning and end of measurement
4: measurement time (min)
6.22: mmol molecular extinction coefficient of NADH
0.5: amount of solution in cuvette (mL)
0.1: amount of protein (mg)

FIG. 13 shows Complex 1 activity for cases where compound 1, 5, 8 or sterile water (control) were added. It can be seen that the Complex 1 activity was maintained when compound 1 or 5 was added compared with the control and compound 8.

Example 6

In this example, compound 1, 5, or 8 was injected into rat midbrain left substantia nigra and the effect thereof was examined.

(1) Either 6 mM of 6-hydroxydopamine (6-OHDA) alone or mixtures of 6 mM of 6-OHDA and 1 mM of each compound was injected into the midbrain left substantia nigra (4.8 mm×1.8 mm, 7.8 mm depth) of rats (Wister rat, male, 250 g). Where the rat was injected with 6 mM of 6-hydroxydopamine (6-OHDA) in midbrain left substantia nigra, the right-side substantia nigra was intact but in the left-side oxidative stress induced the death of dopamine neurons, and the rat rotate in a clockwise direction due to the imbalanced amount of acting dopamine, showing a behavioral abnormality characteristic of Parkinson's disease patients.

After 9 weeks, the rats were injected with methamphetamine (Dainippon Pharma Co., Ltd.), which causes a dopamine release, leading to a release of large amount of dopamine from dopamine neurons into the striatum. Because of the imbalance in the amounts of released dopamine between the left and right substantia nigra the rats started to rotate in a clockwise direction. The rats were placed in a rotameter, and the number of rotations was measured. The total number of rotations over 60 minutes is shown in FIG. 14, and the number of rotations at every 5 minutes over time is shown in FIG. 15.

This figure shows that a decrease in the number of rotations was observed and the behavioral abnormality was suppressed by 55% to 65%, when compound 1 or 5 was injected simultaneously with 6-OHDA. This suppression efficiency is remarkably high, whereas compound 8 did not show such effect. Accordingly, the behavioral abnormality seen in Parkinson's disease was greatly improved by compounds 1 and 5.

(2) The rats subjected to the behavioral abnormality test above were perfused with 50 mL of 10 mM PBS and then with 300 mL of 100 mM phosphate buffer (containing 4% paraformaldehyde, 0.35% glutaraldehyde, and 0.2% picric acid). The midbrain substantia nigra (SNpc) was dissected out and fixed in a 100 mM phosphate buffer containing 4% of paraformaldehyde for 2 days, and then submerged in 100 mM phosphate buffer (containing 15% of sucrose and 0.1% of sodium azide). A 20 μm thick slices were prepared using Cryostat, and submerged in a 100 mM phosphate buffer containing 0.3% Triton X-100 (PBS-T).

These brain slices were reacted with anti-tyrosine hydroxylase (TH: a dopamine-biosynthetic enzyme and marker for dopamine neurons, manufactured by Sigma, 1:20,000 dilution) at 4° C. for 3 days, then washed, and reacted with a biotinylated anti-mouse IgG antibody (1:2,000 dilution) at room temperature for 2 hours. Subsequently, avidin peroxidase coloration was carried out using an ABC kit (Vector Laboratories) at room temperature for 1 hour. After washing several times with PBS-T, coloration was carried out by nickel ammonium-containing 3,3'-diaminobenzidine (DAB). The results are shown in FIG. 16. In the figure, the area stained with black shows the presence of dopamine neurons.

In the left substantia nigra into which only 6-OHDA was injected, TH staining was not observed and thus dopaminergic neuron death was observed. In the right substantia nigra, which was not injected with 6-OHDA, live dopamine neurons were observed (FIG. 16 (1)). However, when the left substantia nigra was injected with compound 1 or 5 simultaneously with 6-OHDA, neuronal death was considerably suppressed (FIG. 16 (2) and (3)). Compound 8 did not have such effect (FIG. 16 (4)).

Accordingly, whereas a low molecular weight compound that binds to the active site of DJ-1 protein (i.e. the region around the cysteine at the 106th residue) had an effect in suppressing neuronal death in human (Example 1), an effect in maintaining mitochondrial complex 1 activity (Example 5), and an effect in improving symptoms characteristic of Parkinson's disease patients in a rat (Example 6). In contrast, compound 7, which has a low strength of binding to the active site of DJ-1 protein, and compound 8, which does not bind to the active site of DJ-1 protein, did not have such effects, indicating that a low molecular weight compound exhibiting more than a certain degree of strength of binding to the DJ-1 active site has an effect in suppressing neuronal death and an effect in treating Parkinson's disease.

BRIEF DESCRIPTION OF DRAWINGS

FIG. 1 A diagram showing a mass spectrum chart of compound 1 (M.W. 291). Needle voltage: 2.4 kV, orifice voltage: 0 V, ring lens voltage: 50 V, ion guide voltage: 3 V, mobile phase solvent: $CHCl_3$:MeOH=4:1. The measured value was larger than the molecular weight calculated from the structural formula, and this shows a structure in which the lactone ring of the sugar moiety was hydrolyzed to become a carboxylic acid.

FIG. 2 A diagram showing a mass spectrum chart of compound 2 (M.W. 329). Needle voltage: 3.24 V, orifice voltage: 0 V, ring lens voltage: 60 V, ion guide voltage: 3 V, mobile phase solvent: $CHCl_3$. The molecular weight and the measured value were in agreement.

FIG. 3 A diagram showing a mass spectrum chart of compound 3 (M.W. 289). Needle voltage: 2 V, orifice voltage: 0 V, ring lens voltage: 50 V, ion guide voltage: 3 V, mobile phase solvent: MeOH. A peak where sodium ion was attached to the compound (289+23=312) was observed.

FIG. 4 A diagram showing a mass spectrum chart of compound 4 (M.W. 312). Needle voltage: 3.4 V, orifice voltage: 0 V, ring lens voltage: 50 V, ion guide voltage: 3 V, mobile phase solvent: $CHCl_3$:MeOH=4:1. The molecular weight and the measured value were in agreement.

FIG. 5 A diagram showing a mass spectrum chart of compound 5 (M.W. 450). Needle voltage: 3.24 V, orifice voltage: 0 V, ring lens voltage: 60 V, ion guide voltage: 3 V, mobile phase solvent: $CHCl_3$. The molecular weight and the measured value were in agreement.

FIG. 6 A diagram showing a mass spectrum chart of compound 6 (M.W. 505). Needle voltage: 2 V, orifice voltage: 0 V, ring lens voltage: 80 V, ion guide voltage: 3 V, mobile phase solvent: MeOH. A peak where sodium ion was attached to the compound (505+23=528) was observed.

FIG. 7 A diagram showing a mass spectrum chart of compound 7 (M.W. 391). Needle voltage 2 V, orifice voltage: 0 V, ring lens voltage: 50 V, ion guide voltage: 3 V, mobile phase solvent: MeOH. A peak where sodium ion was attached to the compound (391+23=414) was observed.

FIG. 8 A diagram showing a mass spectrum chart of compound 8 (M.W. 604). Needle voltage: 3.24 V, orifice voltage: 0 V, ring lens voltage: 60 V, ion guide voltage: 3 V, mobile phase solvent: $CHCl_3$. The molecular weight and the measured value were in agreement.

FIG. 9 A diagram showing the effect of test compounds in suppressing cell death.

FIG. 10 A diagram showing the effect of test compounds in eliminating hydrogen peroxide in cells.

FIG. 11 A diagram showing change in frequency for test compounds using an AffinixQ.

FIG. 12 A diagram showing the effect of test compounds in suppressing DJ-1 oxidation.

FIG. 13 A diagram showing the effect of test compounds in maintaining Complex 1 activity.

FIG. 14 A diagram showing a total number of rotations of model rats 60 in minutes after injection with DJ-1-binding compounds.

FIG. 15 A diagram showing the number of rotations of model rats every 5 minutes over time after injection with DJ-1-binding compounds.

FIG. 16 Shows a photograph of staining with TH (dopamine neuron marker) of rat midbrains injected with 6-OHDA and DJ-1-binding compounds. The injected left substantia nigra is shown in left-side, and the normal right substantia nigra is shown in right-side. The rectangles on the right show enlarged photographs of the left substantia nigra.

The invention claimed is:

1. A method for treating Parkinson's disease using a compound with a binding energy to the active site of DJ-1 protein being −60 kcal/mol or below, wherein the compound is represented by the following Formula:

[Chem. 3]

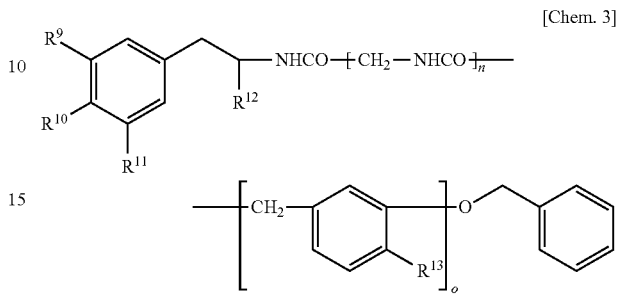

wherein, $R^9$ to $R^{11}$ may be identical to or different from each other, and denote a hydrogen atom, a hydroxy group, an alkoxy group, an aryloxy group, an acyloxy group (—O—CO—$R^{14}$, $R^{14}$ denotes an alkyl group having 1 to 6 carbons or an aryl group) or a sulfonyloxy group (—O—$SO_2$—$R^{15}$, $R^{15}$ denotes an alkyl group having 1 to 6 carbons or an aryl group), or alternatively $R^9$ and $R^{13}$ may together form the following Formulae:

[Chem. 2]

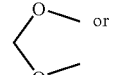 (1)

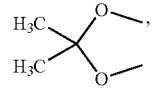 (2)

$R^{12}$ denotes a hydrogen atom or —(CONH)p$R^{16}$ (wherein $R^{16}$ denotes an alkyl group, an aryl group or —CH($CONH_2$)$_q$($CH_2SO_2NH_2$)$_r$($CH_2CH(CH_3)_2$)$_s$ (wherein, q, r and s denote integers of 0 to 2 that satisfy q+r+s=2), and p denotes 1 or 2), $R^{13}$ denotes a hydrogen atom, a hydroxy group, or an alkoxy group, n denotes an integer of 0 to 2, o denotes 0 or 1, and n+o=1 or 2.

2. A method for treating a subject suffering from Parkinson's disease, comprising administering to the subject a compound with a binding energy to the active site of DJ-1 protein being −60 kcal/mol or below, wherein the compound is represented by the following Formula:

[Chem. 3]

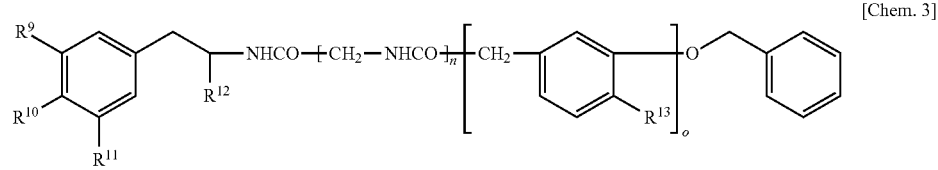

wherein, $R^9$ to $R^{11}$ may be identical to or different from each other, and denote a hydrogen atom, a hydroxy group, an alkoxy group, an aryloxy group, an acyloxy group (—O—CO—$R^{14}$, $R^{14}$ denotes an alkyl group having 1 to 6 carbons or an aryl group) or a sulfonyloxy group (—O—SO$_2$—$R^{15}$, $R^{15}$ denotes an alkyl group having 1 to 6 carbons or an aryl group), or alternatively $R^9$ and $R^{10}$ may together form the following Formulae:

[Chem. 2]

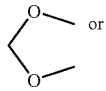 or (1)

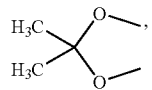

(2)

$R^{12}$ denotes a hydrogen atom or —(CONH)p$R^{16}$ (wherein $R^{16}$ denotes an alkyl group, an aryl group or —CH(CONH$_2$)$_q$(CH$_2$SO$_2$NH$_2$)$_r$(CH$_2$CH(CH$_3$)$_2$)$_s$ (wherein, q, r and s denote integers of 0 to 2 that satisfy q+r+s=2), and p denotes 1 or 2), $R^{13}$ denotes a hydrogen atom, a hydroxy group, or an alkoxy group, n denotes an integer of 0 to 2, o denotes 0 or 1, and n+o=1 or 2.

* * * * *

UNITED STATES PATENT AND TRADEMARK OFFICE
CERTIFICATE OF CORRECTION

PATENT NO.       : 8,318,798 B2
APPLICATION NO.  : 12/085424
DATED            : November 27, 2012
INVENTOR(S)      : Hiroyoshi Ariga It is certified that error appears in the above-identified patent and that said Letters Patent is hereby corrected as shown below:

On the cover page:

Item (73) Assignee should read: National University Corporation Hokkaido University, Hokkaido (JP)

Signed and Sealed this
Twenty-sixth Day of February, 2013

Teresa Stanek Rea
*Acting Director of the United States Patent and Trademark Office*